(12) United States Patent
Erman et al.

(10) Patent No.: US 10,874,347 B1
(45) Date of Patent: Dec. 29, 2020

(54) MULTIPLE PLANE SENSORS

(71) Applicant: Focal Wellness, Inc., Carlsbad, CA (US)

(72) Inventors: Randal Erman, San Marcos, CA (US); John L. Thompson, Cota de Cave, CA (US); Mark Bowles, La Jolla, CA (US)

(73) Assignee: Focal Wellness, Inc., Carlsbad, CA (US)

(*) Notice: Subject to any disclaimer, the term of this patent is extended or adjusted under 35 U.S.C. 154(b) by 230 days.

(21) Appl. No.: 15/909,952

(22) Filed: Mar. 1, 2018

Related U.S. Application Data

(60) Provisional application No. 62/465,829, filed on Mar. 2, 2017.

(51) Int. Cl.
*A61B 5/00* (2006.01)
*A61B 5/11* (2006.01)

(52) U.S. Cl.
CPC .......... *A61B 5/6831* (2013.01); *A61B 5/1126* (2013.01)

(58) Field of Classification Search
CPC ............................ A61B 5/6831; A61B 5/1126
USPC ...................................................... 73/379.01
See application file for complete search history.

(56) References Cited

U.S. PATENT DOCUMENTS

| | | | |
|---|---|---|---|
| 4,774,966 A | 10/1988 | Lemmen | |
| 4,850,341 A | 7/1989 | Fabry et al. | |
| 5,031,640 A | 7/1991 | Spitzer | |
| 5,501,657 A | 3/1996 | Feero | |
| 5,676,476 A | 10/1997 | Uke | |
| 5,851,191 A | 12/1998 | Gozani | |
| 6,006,751 A | 12/1999 | Spitzer | |
| 6,045,517 A | 4/2000 | Williams | |
| 6,179,852 B1 | 1/2001 | Strickland et al. | |
| 6,510,346 B2 | 1/2003 | Gordon | |
| 6,530,893 B1 | 3/2003 | Castelli | |
| 6,852,067 B2 | 2/2005 | Limonadi | |
| 6,893,396 B2 | 5/2005 | Schulze et al. | |
| 7,344,511 B2 | 3/2008 | Porrata et al. | |
| 7,364,559 B2 | 4/2008 | Williams | |
| 7,834,851 B1 | 11/2010 | Fidali et al. | |
| 7,942,918 B2 | 5/2011 | Herzberg et al. | |
| 8,942,662 B2* | 1/2015 | Pan | G08B 21/02 455/404.1 |
| 9,223,956 B2 | 12/2015 | Hong et al. | |
| 9,387,109 B2 | 7/2016 | Keoshian et al. | |
| 9,808,208 B1* | 11/2017 | Erman | A61B 5/0022 |
| 2002/0140674 A1 | 10/2002 | Okuno et al. | |

(Continued)

OTHER PUBLICATIONS

International Search Report for PCT/US2017/058516 dated Feb. 21, 2018.

*Primary Examiner* — Jamel E Williams
(74) *Attorney, Agent, or Firm* — Clause Eight IPS; Michael Catania

(57) ABSTRACT

A series of multi-plane sensors are attached to different points on the body such as forearms, calves, lower backs, and necks and are used to establish planes of each body part is disclosed herein. The multi-plane sensors stream the plane data and velocity vector data to a centralized computing device such as a computer, smart phone, or smart watch. The centralized computing device runs a software application which includes an open source library which platform partners utilize to write proprietary applications which utilize the sensor stream data.

3 Claims, 6 Drawing Sheets

(56) References Cited

U.S. PATENT DOCUMENTS

| | | | |
|---|---|---|---|
| 2005/0250996 A1* | 11/2005 | Shirai | A61B 3/113 600/301 |
| 2006/0004302 A1 | 1/2006 | Tuckett et al. | |
| 2007/0156158 A1 | 7/2007 | Herzberg et al. | |
| 2008/0181917 A1 | 7/2008 | Pappagallo et al. | |
| 2008/0204225 A1 | 8/2008 | Kitchen | |
| 2009/0062707 A1 | 3/2009 | Busuttil | |
| 2009/0143704 A1 | 6/2009 | Bonneau et al. | |
| 2011/0033830 A1 | 2/2011 | Cherian | |
| 2011/0208100 A1 | 8/2011 | Eck et al. | |
| 2011/0230805 A1 | 9/2011 | Oron | |
| 2012/0317693 A1 | 12/2012 | Hatz | |
| 2013/0190903 A1* | 7/2013 | Balakrishnan | G09B 5/125 700/91 |
| 2013/0217352 A1* | 8/2013 | Pan | G08B 21/02 455/404.1 |
| 2013/0317648 A1* | 11/2013 | Assad | G06F 3/015 700/258 |
| 2014/0236059 A1 | 8/2014 | Son | |
| 2014/0240223 A1* | 8/2014 | Lake | G06F 3/011 345/156 |
| 2014/0296760 A1 | 10/2014 | Keoshian et al. | |
| 2014/0343473 A1 | 11/2014 | Hoffman | |
| 2015/0153374 A1* | 6/2015 | Balakrishnan | G04G 21/00 702/178 |
| 2015/0306373 A1 | 10/2015 | Bouton et al. | |
| 2016/0015280 A1 | 1/2016 | Hyde et al. | |
| 2016/0296406 A1 | 10/2016 | Heyl | |
| 2017/0148282 A1* | 5/2017 | Granlund | G06F 3/016 |
| 2017/0156662 A1 | 6/2017 | Goodall et al. | |
| 2017/0164876 A1 | 6/2017 | Hyde et al. | |
| 2017/0196513 A1* | 7/2017 | Longinotti-Buitoni | A61B 5/743 |
| 2018/0116587 A1* | 5/2018 | Erman | A61B 5/6806 |

* cited by examiner

MULTIPLE PLANE SENSORS

CROSS REFERENCE TO RELATED APPLICATION

The present application claims priority to U.S. Provisional Patent Application No. 62/465,829 filed on Mar. 2, 2017, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to devices for training proper positioning.

Description of the Related Art

Many injuries are caused by improper positioning when performing an action.

BRIEF SUMMARY OF THE INVENTION

One aspect of the present invention is a system for monitoring a desired body motion. The system comprises a plurality of sensor articles. Each of the plurality of sensor articles comprises a body configured to be worn by a user, a single sensor or plurality of sensors, a processor, a wireless transceiver, a vibration mechanism, and a power source. The plurality of sensors monitors a motion of the user. The processor of the article is configured to determine if the user's motion is desired and the processor is configured to send alerts via the vibration mechanism at programmatic sequences of the motion.

Another aspect of the present invention is a system for monitoring a desired body motion. The system comprises a computing device and a plurality of sensor articles. Each of the plurality of sensor articles comprises a body configured to be worn by a user, a single sensor or plurality of sensors, a processor, a wireless transceiver, and a power source. The device comprises a display screen, a processor, a wireless transceiver, and a software application. The plurality of sensors monitors a motion of the user. The processor of the article is configured to determine if the user's motion is desired and the processor is configured to transmit an alert signal for transmission from the wireless transceiver of the article. The alert signal is received at the wireless transceiver of the device and the application is configured to notify a user via the display screen regarding the non desirable motion.

Yet another aspect of the present invention is a method for monitoring desirable body motion. The method includes monitoring a motion of the user using a plurality of sensor articles. Each of the plurality of sensor articles comprises a body configured to be worn by a user, a single sensor or plurality of sensors, a processor, a wireless transceiver, and a power source. The method also includes determining that the user's motion is desirable from a signal from the plurality of sensor articles. The method also includes transmitting an alert signal from a wireless transceiver of the sensor article. The method also includes receiving the alert signal at a wireless transceiver of a device. The method also includes activating a warning on the device to alert the user to the improper motion.

Yet another aspect of the present invention is a system for monitoring a desired body motion. The system comprises a computing device and a plurality of sensor articles. Each of the plurality of sensor articles comprises a body configured to be worn by a user, a single sensor or plurality of sensors, a processor, a wireless transceiver, and a power source. The device comprises a display screen, a processor, a wireless transceiver, and a software application. The plurality of sensors monitors a motion of the user. The processor of the article is configured to determine if the user's motion adheres to a predetermined training motion and the processor is configured to transmit an alert signal for transmission from the wireless transceiver of the article. The alert signal is received at the wireless transceiver of the device and the application is configured to display a warning on the display screen to alert the user to the improper motion.

The plurality of sensors preferably comprises a single instance or plurality of inertia measurement unit (IMU) sensors. Each of the sensors preferably has an LED for indication of proper positioning. The single instance or plurality of sensors is alternatively comprised of a plurality of piezoelectric bend/flex sensors.

A first sensor article of the plurality of sensor articles is preferably worn on an upper back of the user and a second sensor article of the plurality of sensor articles is worn on a calf of the user and a third article is worn on the waist of the user. Each of the plurality of sensor articles is preferably positioned parallel to the other plurality of sensor articles.

The software application is configured to determine a user's proper motion when the plurality of sensor articles are following the desired motion vector.

The software application is preferably configured to train a set of motion vectors for a user.

The software application is preferably configured to determine a base training motion for a user.

The software application is preferably configured to determine a user's proper motion when the plurality of sensor articles are in alignment with each other.

In one embodiment, the alert signal is an audio alert. In another embodiment, the alert signal is a visual alert.

Alternatively, the plurality of sensor articles comprises a first sensor article, a second sensor article and a third sensor article.

In one embodiment, the article further comprises a vibration mechanism alert.

The system can provide different alert behaviors/attribution based on if the position is desirable. Further the alerts can be sequenced to cause the user to move in a desired manner.

The system further comprises pressure sensors on the bottom of a shoe/boot to show the pressure profile during the motion profile in an attempt to measure balance.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
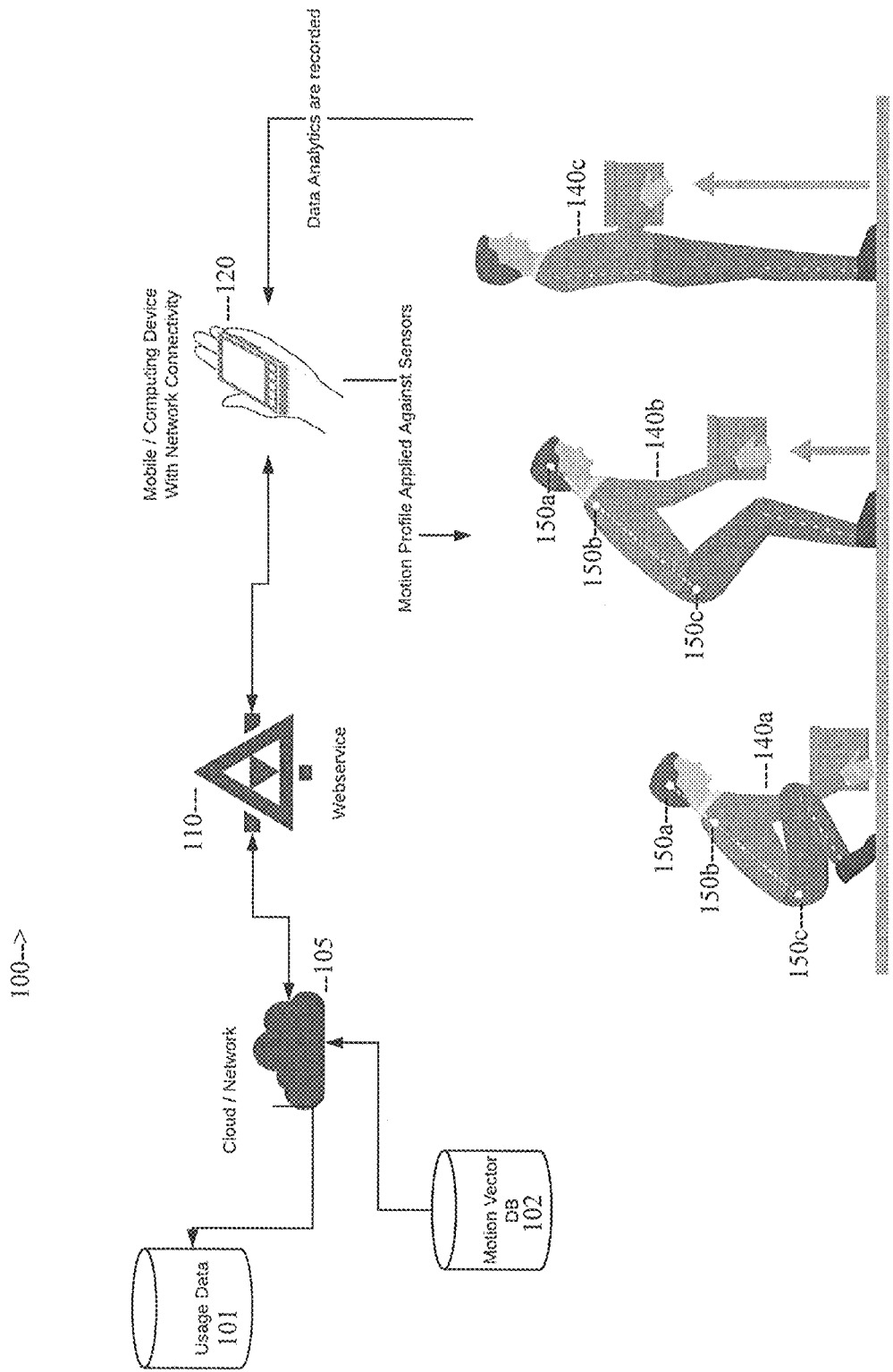
FIG. 1 is a block diagram of a basic usage model for a system for monitoring a desired body motion.

The invention is a series of absolute position sensors which are attached to different points on a user's body such as forearms, calves, lower backs, and necks and are used to establish planes of each body part. These sensors stream the plane data and velocity vector data to a centralized computing system such as a computer, smart phone, or smart watch. The centralized computing system runs an application which may include an open source library which platform partners utilize to write their own applications which utilize the sensor stream data. The use of the sensor data is boundless.

The plane sensor pods themselves are preferably each a sensor which includes a Bluetooth Low Energy Module, an IMU, a Haptic Feedback Mechanism, charging circuit, battery, and LEDS. Alternatively, the sensor pods are each a non vibration board which removes the vibration motor from the board and is smaller in form factor and at a cheaper cost. Alternatively, the sensor pods are each a separate board with a different plurality of sensors which report back to the main computing system or via a wireless mesh. The centralized computing system preferably includes the sensor data needed to be considered one of the plurality of sensors.

The centralized computing system preferably connects to all the plane sensors concurrently directly or via a mesh or if there are more plane sensors then the host wireless technology can handle at once software will switch between different sensors to collect the data in a TDMA fashion. The plane sensors are able to cache some amount of data while the host device is cycling through to other devices.

The plane sensors are preferably attached directly to skin either via an adhesive or be held within a band or a sleeve, which is worn by the user. The plane sensors further are not limited to tracking human motion. These sensors and corresponding attachment mechanisms are preferably utilized for mechanical, animal, or robotic motion monitoring.

The sensors and signal processing algorithm include a tunable mean, average, and root mean squared signal processing for data returned by the IMU.

The LEDs of the sensor is configured to display different states of the radio (searching, connected, etc), and also different states of that plane as reported back by the central processing unit.

The system has the ability to be "trained" in a given pattern, or preprogrammed pattern, such that if there are three sensors A, B, C, are trained in TrainedPatternVectorA, TrainedPatternVectorB, TrainedPatternVectorC when a user is asked to repeat the vector pattern that the sensors detect if the pattern was recreated correctly. The system has the ability to add a customizable tolerance factor, or allowed difference from the TrainedPatternVector and the ActualPatternVector. The Vibration sensor and or a potential audio sensor then give positive or negative indications if the difference between the vectors was within the tolerance.

Another operation of the system is a preprogrammed motion vector for all sensors, such that when a user is using the sensors and does not follow the preprogrammed vector motion a plurality of alerts notify the user of which plane is not within the tolerance of motion.

The system platform also includes the ability to count how many successful and unsuccessful times a person has accomplished the motion as described by the training program.

The system shall support a configurable timeframe where the sensors are reporting a desired position before an alert is activated.

The system shall support multiple patterns which can be utilized by the central computing device. The use case here would be a gym where someone is lifting weights in a certain way and then has to go and do leg lifts which is a different motion.

The ability for the system to take data from two distinct plane sensor setups and merge the data into one virtual process. Imagine two fencing players who both have plane sensors and want to recreate the match in 3D space by taking the stored vector data and then aligning the timestamps such that the vector data(a)T==vector data(b)T.

It should be further noted that the planes sensor array can be run with or without the centralized computing system once trained. If the planes sensor array are still connected while an actual pattern is being executed against a trained pattern an overlay of the difference can be displayed to the user as a difference over time chart.

Example applications of the planes platform include an athletic trainer who wants to make sure that people who are doing lifting exercises correctly. They may after setting up a "training path" for the sensors of a proper lift may then set a goal of 50 proper lifts which is then counted by the central processing system such as a computer, smart phone or smart watch.

Another example is a tennis instructor who sets up a training path, but after a certain amount of successful times achieving the training path within a given tolerance the tolerance is automatically decreased to increase the precision needed by the human following the path, hence reinforcing the optimal path.

Another example is a sports instructor who affixes three sensors to the head, back, and back of leg to show a proper sports posture for a student. The sports instructor after locking in the correct position then sends the student off to a sporting range where the haptic feedback instructs the student that the position is incorrect and to return to the correct position.

The platform also comes with the software which allows developers a quick and easy way to correlate the position of a sensor to a body form.

In this way a user can then overlay the image of the individual over a 3-dimensional stick figure which binds to the 2-dimensional image. That 2-dimensional image is then manipulated in the 3-dimensional space. This could be considered a poor mans green screen. This motion is captured for a static image and also a 3-dimensional motion of vectors which are recorded and applied to the 3-dimensional space in the green screen.

This planes system also includes the capability to have the centralized computing system send processed and non-processed data to the cloud (i.e. remote database) such that the data can be viewed or processed at a later time by applications.

The planes platform includes a downloadable opensource library which others can use to build their own applications which use the plane sensors.

The planes system although currently designed with a vibration motor as feedback may include an audio circuit as well, and or the vibration motor may be replaced by an audio circuit.

The preferred wireless technology is bluetooth low energy, but wife, uwb, wusb, zigbee are other possible radio technologies that this system can be built with.

The charging circuit can be either a direct connect via a plug, or usb cable, and or an inductive charging circuit.

The sensor articles are preferably composed of rigid material or flexible material based on consumer preferences.

The system preferably utilizes both wired and wireless means of communication with a host system to provide data to the application software.

In one embodiment, the system comprises a microprocessor, a wireless chipset such as WiFi, BT, BTLE, UWB or NFC, a plurality of 10 Degree of Freedom (DOF) sensor technology (Gyroscopes), and a battery.

In an alternative embodiment, the system comprises a microprocessor, a wireless chipset such as WiFi, BT, BTLE, UWB or NFC, a plurality of accelerometers, and a battery.

The system can also include a charging circuit depending upon which type of battery technology is incorporated.

The system can also include LEDs to indicate if the user is in a proper position.

The system can also include LEDs to indicate the state of the power circuit and battery power level.

The system can also include a sound buzzer which can be utilized to give extra feedback to the consumers about the desired motions.

The system can also include a shaking/motion device to give physical feedback in terms of correct or incorrect motions.

The system can be configured with any number of IMUs directly integrated onto the same board as the microprocessor, or a subset of IMUs directly integrated onto the same board as the microprocessor and remaining subset connected to that board in some fashion, or all IMUs connected to the microprocessor board in some fashion.

The system can also be made up of a microprocessor with embedded wireless technology such as WiFi, BT, BTLE, UWB, or NFC, and the needed sensor technology.

The system sensor technology can include any combination of the following depending on the information required: 0 or more IMUs, 0 or more force sensors, 0 or more push buttons/switches, and 0 or more strain sensors.

The system host software receives data from a sensor article that can have already been fully processed or retrieve partially processed or raw data from the device.

The system data reporting is to the consumer via an application, or bypasses the consumer and goes directly into a cloud database, and/or goes to the consumer via an application as well as goes into a cloud database.

Software running on the host system can be configured to run in endless capture mode where all data is stored to the cloud database. The software system can also be configured to cache the data in the case the system is offline and needs to sync to the database at a later time.

The system platform includes a mechanism to store all data to a cloud database for further processing and analytics.

The system software detects when user input has occurred and catalogs RSSI values. Those RSSI values are then included in the algorithm to determine if data processing should occur.

Utilizing the above mentioned software algorithm to train users to the desired motions.

The system preferably uses the accelerometer data to compute the angle. In reality the system is made of an accelerometer, and some number of gyros/compass sensors which can be used to create pitch and yaw.

The BTLE device is preferably a Silicon Labs 121BLE.

FIG. 1 is a block diagram of a basic usage model for a system 100 for monitoring a desired body motion. The system 100 preferably comprises a computing device 120, a web-service 110, a usage database 101, a motion vector database 102, and a plurality of sensor articles 150*a*, 150*b* and 150*c* attached to a person 140*a*. As the person lifts a box from a first position 140*a* to a second position 140*b* to a third and final position 140*c*, data is sent from the sensor articles 150*a*, 150*b* and 150*c* to the computing device 120, to the web-service 110, and to the usage database 101.

Figure 2:
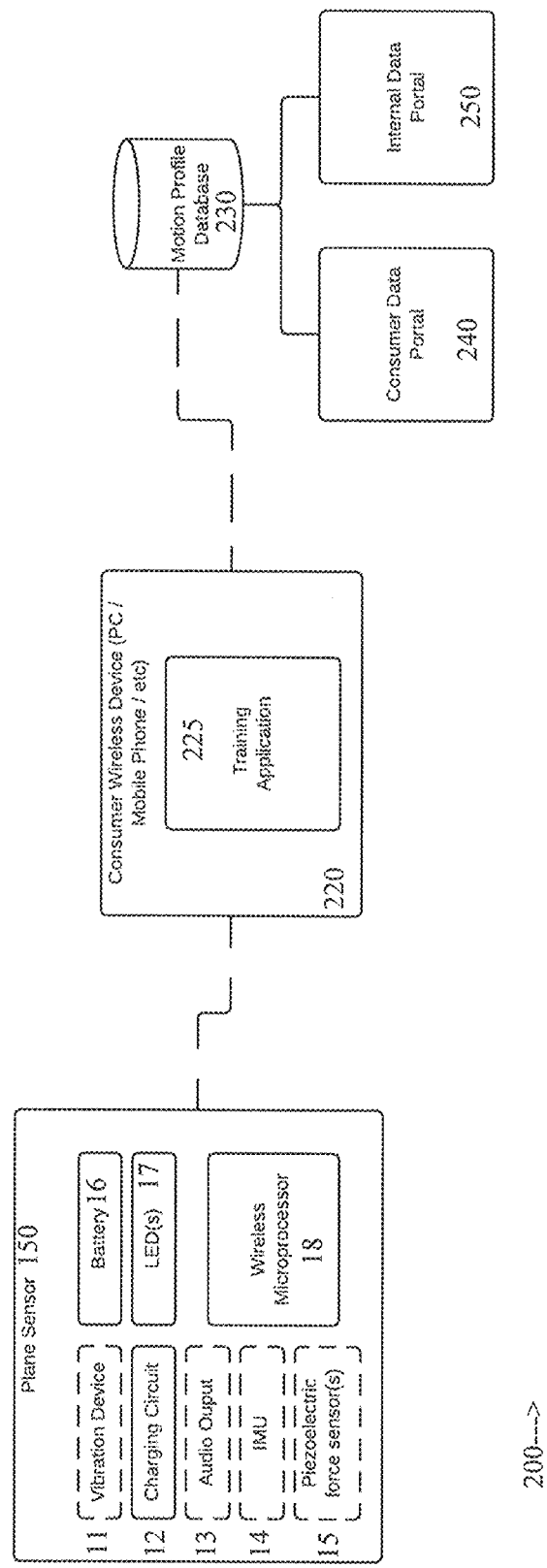
FIG. 2 is a block diagram for a system for monitoring a desired body motion.

FIG. 2 is a block diagram for a system 200 for monitoring a desired body motion. The system preferably comprises a plane sensor 150, a computing device 220, a motion profile database 230, a consumer data portal 240 and an internal data portal 250. The plane sensor 150 preferably comprises a vibration device 11, a charging circuit 12, an audio output 13, an IMU 14, a piezoelectric force sensor 15, a battery 16, LEDs 17 and a wireless processor 18. The components of the plane sensor 150 are preferably enclosed in a housing configured to be affixed to a person's body. The computing device preferably is a smartphone having a training application 225.

Figure 3:
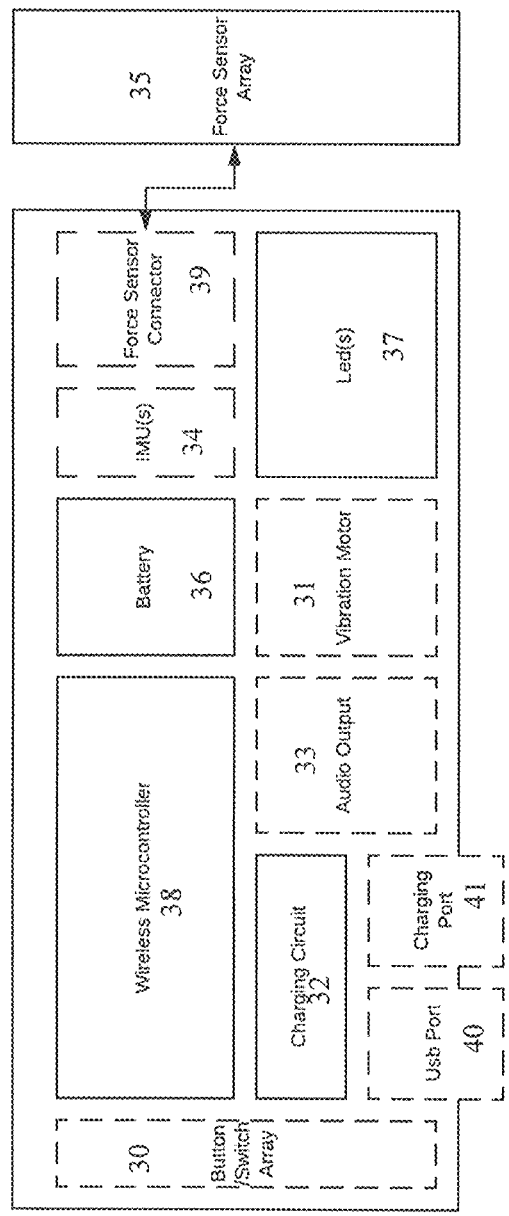
FIG. 3 is a block diagram of a plane sensor for a system for monitoring a desired body motion.

FIG. 3 is a block diagram of a plane sensor 300 for a system for monitoring a desired body motion. The plane sensor 300 preferably comprises a switch array 30, a vibration device 31, a charging circuit 32, an audio output 33, an IMU 34, a force sensor array 35, a battery 36, LEDs 37, a wireless processor 38, a force sensor connector 39, a USB port 40 and a charging port 41. The components of the plane sensor 150 are preferably enclosed in a housing configured to be affixed to a person's body.

Figure 4:
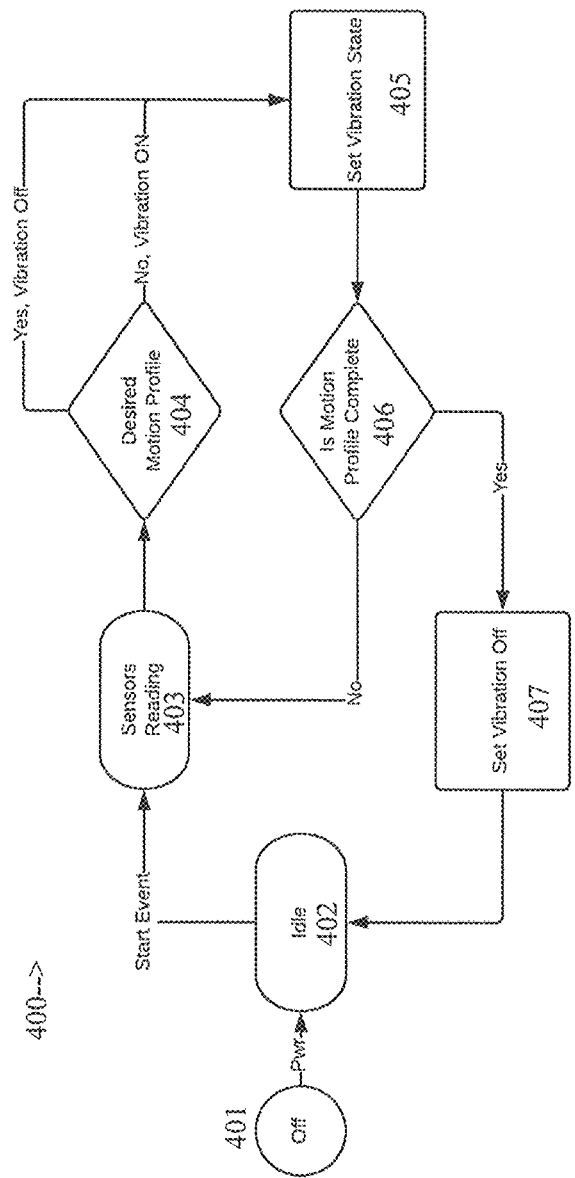
FIG. 4 is a flow chart for a method for monitoring a desired body motion.

FIG. 4 is a flow chart for a method 400 for monitoring a desired body motion. At circle 401, the sensor is off. At block 402, the sensor is in idle. At block 403, the sensor begins reading the movement of the user. At inquiry 404, the processor determines if the person is moving in a desired motion profile. If yes, then no vibration. If no, then a vibration and at block 405 the vibration state is state. At inquiry 406, the processor determines if the motion profile is complete. If no, the method returns to block 403 to continue sensor readings. If yes, at block 407 the vibration is set to off and the sensor returns to an idle state at block 402.

Figure 5:
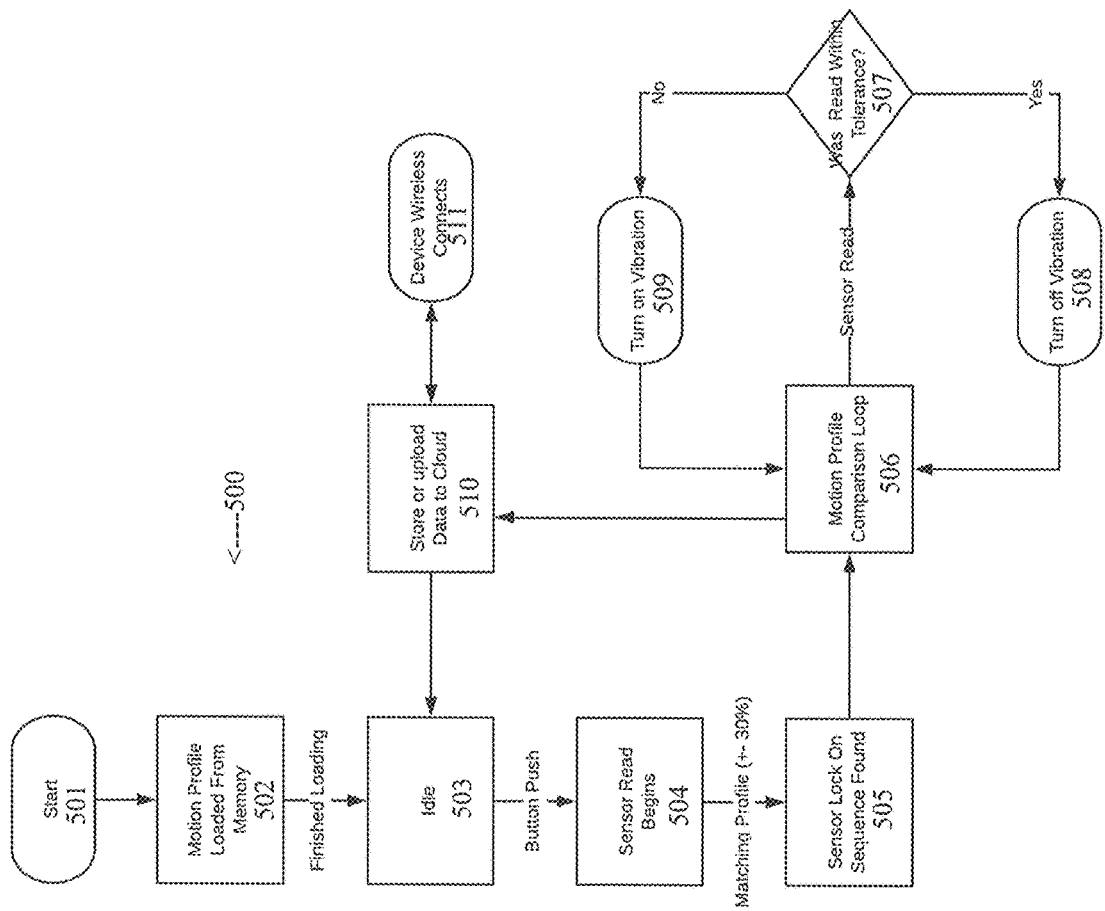
FIG. 5 is a flow chart for a method for monitoring a desired body motion.

FIG. 5 is a flow chart for a method 500 for monitoring a desired body motion. The method begins at block 501. At block 502, a motion profile is loaded from a memory. At block 503, the sensor is idle. A button is pushed and at block 504 the sensor begins monitoring the user. At block 505, a sensor lock on sequence is found. A block 506, a motion profile comparison loop begins. At inquiry 507, the processor determines if the sensor reading was within a predetermined tolerance. If yes, at block 508 the vibration is turned off. If no, at block 509 the vibration mechanism is activated. At block 510, the data is sent to the cloud to upload and store at a remote database. At block 511, a device connects wirelessly to the cloud for output.

Figure 6:
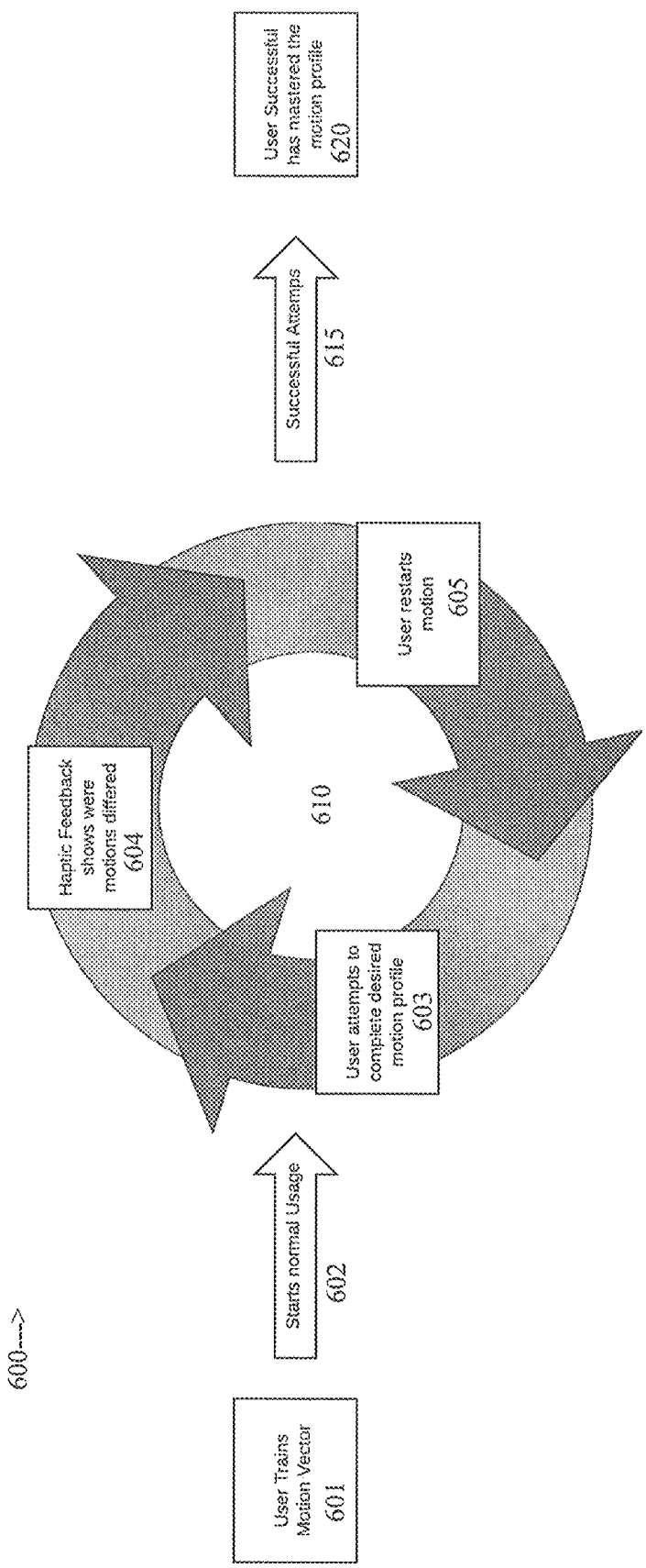
FIG. 6 is a flow chart for a repetition method for monitoring a desired body motion.

FIG. 6 is a flow chart for a repetition method 600 for monitoring a desired body motion. At block 601, a user trains a motion vector. At block 602, a user starts normal usage. In a repetition circle 610, at block 603, a user attempts to complete a desired motion profile. At block 604, haptic feedback shows were motions differ between the profile and the usage. At block 605, the user restarts the desired motion. At block 615, the user has made successful attempts at the desired motion. At block 620, the user has successfully mastered the motion profile.

Erman, U.S. Pat. No. 9,808,208 for a Carpal Tunnel Infomatic Monitor is hereby incorporated by reference in its entirety.

Erman, U.S. patent application Ser. No. 15/802,420, filed on Nov. 2, 2017, for a Cubital Tunnel Infomatic Monitor is hereby incorporated by reference in its entirety.

Erman, U.S. patent application Ser. No. 15/890,704, filed on Feb. 7, 2018, for a Method And System For Proper Kicking Technique is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A method for monitoring desirable body motion, the method comprising:

monitoring a motion of the user using a plurality of sensor articles, each of the plurality of sensor articles comprising a body configured to be worn by a user, a plurality of sensors, a processor, a wireless transceiver, and a power source, each of the plurality of sensors is an inertia measurement unit (IMU) sensor or a piezo electric flex sensor which can bend detect angle;

determining that the user's motion is desirable from a signal from the plurality of sensor articles;

transmitting an alert signal from a wireless transceiver of the sensor article;

receiving the alert signal at a wireless transceiver of a device; and activating a warning on the device to alert the user to the improper motion;

wherein combining the plurality of sensor articles via a wireless domain using an initial calibration phase and then continuous feedback through the system, the noise from each sensor of the plurality of sensors is dampened to allow for a continuous accurate vector resolution.

2. The method according to claim 1 wherein the software application is configured to determine a user's proper motion when the plurality of sensor articles are following the desired motion vector.

3. The method according to claim 1 wherein the software application is configured to determine a base motion for a user.

* * * * *